United States Patent [19]
Zdarsky

[11] 3,962,791
[45] June 15, 1976

[54] STOP FOR THE SHAFT OF A ROOT-CANAL INSTRUMENT

[76] Inventor: Eduard Zdarsky, Brautigamstr. 5, 8 Munich 71, Germany

[22] Filed: Jan. 22, 1975

[21] Appl. No.: 542,933

[30] Foreign Application Priority Data
Jan. 29, 1974   Germany............................ 2404151

[52] U.S. Cl. .................................................. 32/57
[51] Int. Cl.² ........................................... A61C 5/02
[58] Field of Search ............................. 32/57, 40 R

[56] References Cited

UNITED STATES PATENTS

| | | | |
|---|---|---|---|
| 1,035,239 | 8/1912 | Rosenthal ........................... | 32/57 X |
| 1,417,237 | 5/1922 | Evans ................................. | 32/40 R |

*Primary Examiner*—Robert Peshock
*Attorney, Agent, or Firm*—Karl F. Ross; Herbert Dubno

[57] ABSTRACT

A stop to prevent the insertion of the shaft of a root-canal instrument too far into a tooth comprises a housing formed with a throughgoing passage and a compression spring in the passage having an inner diameter smaller than the outer diameter of the shaft. This stop is slipped over the shaft and the spring tightly grasps the shaft so as to impede sliding of the stop therealong. The compression spring may be loosely received within a chamber formed within the housing, or may be imbedded in a block of synthetic-resin material constituting the housing. A two-part housing may be used one part of which is connected to one end of the spring and the other part of which is connected to the other end of the spring so that rotation of these two parts relative to each other allows the spring to be loosened from the shaft to allow easy sliding of the stop therealong.

10 Claims, 8 Drawing Figures

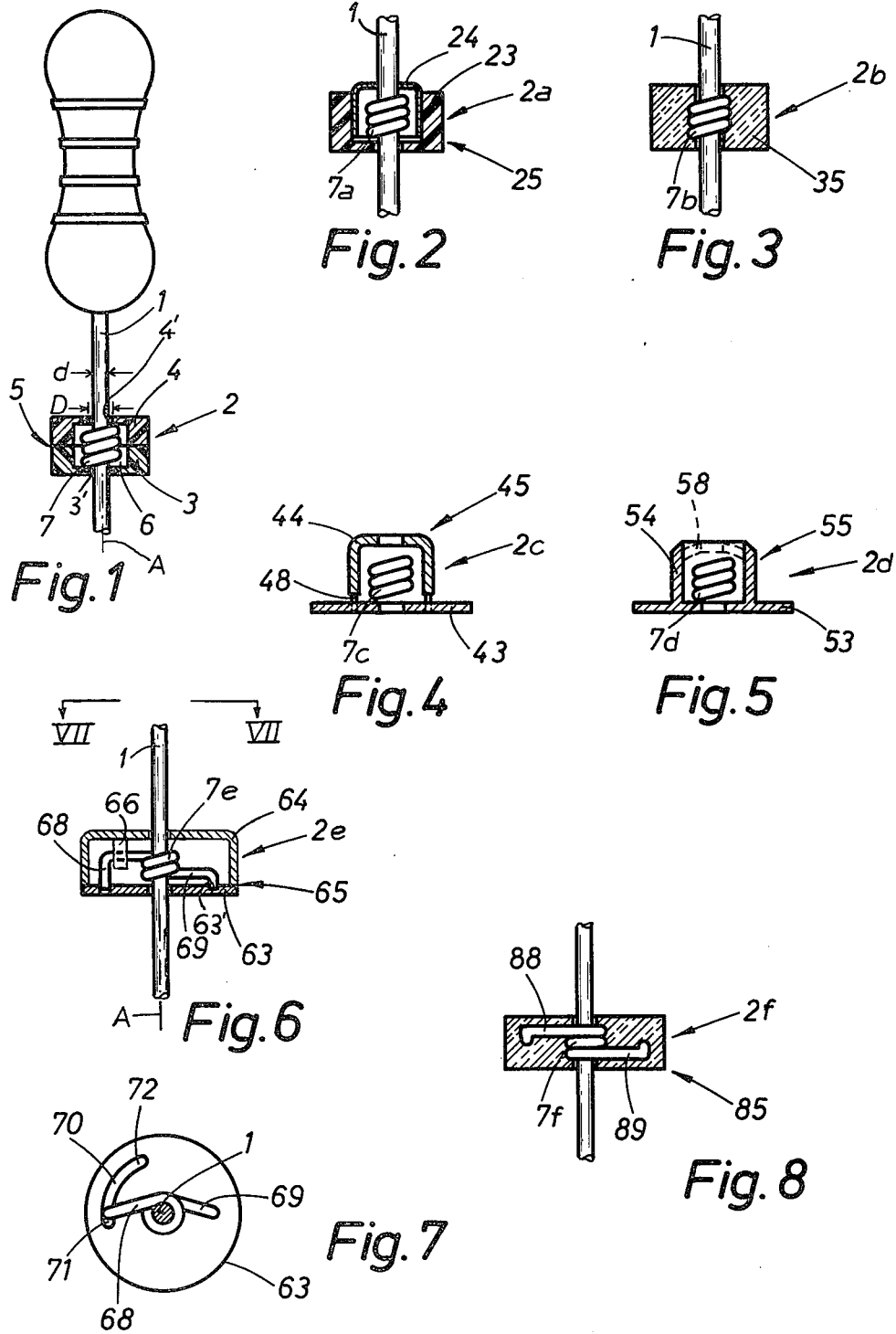

STOP FOR THE SHAFT OF A ROOT-CANAL INSTRUMENT

CROSS-REFERENCE TO RELATED APPLICATION

This application is related to my copending and commonly filed application Ser. No. 542,933 of 22 Jan. 1975.

1. Field of the Invention

This invention concerns an adjustable stop for a root-canal tool. More particularly this invention concerns a device which can be set at any position along the shaft or stem of a root-canal instrument.

2. Background of the Invention

Root-canal work is often carried out with an instrument whose shaft is inserted into the root-canal of the tooth. This shaft has a diameter in the neighborhood of 1 mm and it is absolutely essential that the tip of the shaft not be pushed entirely through the tooth. The possibility of infection or damage to important structures as a result of piercing the instrument through the bottom of the root is considerable.

Thus it is the practice to ascertain, usually by means of an X-ray, how far into the tooth root the stem or shaft can be inserted. Then a stop is placed on the shaft of the root-canal instrument so that the dentist has a handy gauge as to how far in he can insert his instrument. This stop is usually a small and inexpensive disk between 1 and 2 mm thick made of a heat-resistant synthetic-resin or silicone rubber. The disk is formed with a throughgoing hold having a diameter slightly inferior to that of the normally cylindrical shaft so that this stop is deformed when the shaft is inserted through it and therefore rests tightly against it.

A principal disadvantage of such a stop is that it readily becomes loose. Thus it is possible for it to be displaced up the shaft, toward the handle of the instrument, so that the tool is indeed poked out the bottom of the tooth root.

It has also been suggested to provide a more rigidly securable stop which comprises a small metallic disk having a tiny set screw that allows the disk to be tightly clamped to the shaft. Such an arrangement, although having the advantage that it does not slip on the shaft unless a great deal of force is exerted against it, has the considerable disadvantage that it requires the dentist to use a screwdriver or Allen wrench to set the stop. Thus the overall working speed is reduced. In addition such arrangements are relatively expensive so that they must be sterilized and reused.

OBJECTS OF THE INVENTION

It is therefore an object of the present invention to provide an improved stop arrangement for a root-canal instrument.

Yet another object is the provision of such a stop which is relatively inexpensive but which engages the shaft of the root-canal tool very snugly.

A further object is the provision of such a device which requires no tools for its tightening on the shaft.

SUMMARY OF THE INVENTION

These objects are attained according to the present invention in a stop for a root-canal instrument which comprises a container or abutment element formed with a throughgoing hole of larger diameter than the shaft and having an abutment face. The hole defines an axis perpendicular to the face. A compression spring which is secured to the element and has a throughgoing passage aligned with the axis is provided on the element and has a normal inside diameter smaller than that of the shaft. Thus when the shaft is fitted axially through the stop it is tightly gripped by the compression spring. In this manner it is possible for the arrangement to grasp the shaft very tightly so that only a concerted effort can move it along the shaft. At the same the use of a spring-steel compression spring which is not stressed beyond its elastic limit ensures that the stop will not loosen up once mounted on the shaft.

According to yet another feature of this invention the compression spring is received within a block of synthetic-resin or similar material constituting the abutment element.

In accordance with another feature of this invention the compression spring has a pair of ends extending generally radially or tangentially from the general cylindrical body of the spring. These ends can be imbedded in a synthetic-resin block, or a two-part housing, one part of which constitutes the abutment element may be provided. With a two-part housing one part is connected to the one arm and another to the other arm so that rotation of these parts relative to each other in one sense increases the inner diameter of this spring and allow it readily to be mounted on the shaft.

According to yet another feature of this invention the spring is received in a compartment formed in or by metallic housing. This housing may constitute itself the abutment element or may be imbedded in a block of synthetic resin or similar material.

The arrangement according to the present invention can be produced at very low cost. Indeed it can be made so inexpensive that after use it can be simply thrown away. Furthermore it very tightly engages the shaft of the root-canal instrument so that it will not slip during use and permit injury to the patient. It is mounted on the shaft easily, the dentist simply slipping it over the end and forcing it down the shaft. Alternately as discussed above the two housing parts can be rotated relative to each other to allow it to be slipped with ease over the shaft and secured at any location therealong.

BRIEF DESCRIPTION OF THE DRAWING

The above and other objects, features, and advantages will become more readily apparent from the following description, reference being made to the accompanying drawing in which:

FIG. 1 is an axial section through a stop according to the present invention;

FIGS. 2–6 are similar sections through other stops in accordance with this invention;

FIG. 7 is a section taken along line VII—VII of FIG. 6 with one housing part removed for clarity of view; and FIG. 8 is an axial section to another arrangement according to this invention.

SPECIFIC DESCRIPTION

As is shown in FIG. 1 the shaft 1 of a root-canal tool lies on an axis A that passes through a generally cylindrical stop 2. This stop 2 comprises a housing or abutment element 5 itself constituted by two identical parts 3 and 4 with in-line holes 3' and 4' and together forming a cylindrical chamber 6. A 3-turn coil-type compression spring 7 is held in the chamber 6 of the housing 5 and is centered on the axis A like the holes 3' and 4'. Thus the shaft 1 passes through the center of the spring 7 and through the two holes 3' and 4'. The inner diameter of the coil spring 7 is slightly less than the outer diameter $d$ of the shaft 1, here 1.2 mm. Normally the shaft 1 of these tools is between 0.7 and 1.7 mm. The diameters D of the hole 3' and 4' are slightly greater than the diameter $d$. The housing parts 3 and 4 are made of a polyamide such as nylon and are bonded adhesively together at their planar interface. A gauge as described in my above-cited patent application may be used to position the stop 2 on the shaft 1.

The stop 2a of FIG. 2 has a coil spring 7a received in a housing 25 comprising an outer synthetic-resin body 23 and an inner metal can 24. The can 24 is cup-like and opened downwardly. It is simply forced into the correspondingly cup-shape element 23 with the spring 7a between them.

The stop 2b of FIG. 3 has a simple 3-turn coil spring 7b which is received within a synthetic-resin block 35 of cylindrical shape. The block 35 is elastically deformable. In this arrangement, as in the arrangements of FIGS. 1 and 2, the inner diameter of the spring is between 5% and 15% smaller than the diameter $d$ of the shaft 1.

FIG. 4 shows a stop 2c wherein the coil spring 7c is received in a housing formed by a cup-like part 44 of metal that engages with short pins 48 in a disk 43 that constitutes the abutment face of the stop.

The arrangement of FIG. 5 is similar to that of FIG. 4, but here the housing 55 of the stop 2d is metallic and formed of one piece. The coil spring 7d is received within a tubular extension 54 formed on the flat abutment disk 53. The upper end of this extension 54 is bent over as shown at 58 to contain the spring 7d.

In FIGS. 6 and 7 a stop 2e is shown wherein the coil spring 7e has its ends 68 and 69 extending outwardly from its central cylindrically sleeve-like body. These ends 68 and 69 are bent down toward an abutment disk 63 that is formed with a hole 63' in which the very end of the end section 69 is received and with a part-circular slot 70 centered on the axis A and receiving the very end of end section 68. Normally the end 68 lies in the one end 71 of the slot 70. The other housing part 64 is cup-shaped and is formed with a tab 66 that engages down and around the other leg 68. Thus rotation of this portion 64 relative to the disk 63 twists the arm 68 over to the end 72 of the slide 70 and therefore loosens the spring 7e from the shaft 1. This makes it very easy to move the stop 2e to any desired location along the shaft 1. In this arrangement both of the housing parts 63 and 64 are made of stainless steel so that this device can be sterilized and reused.

The arrangement shown in FIG. 8 is similar in principle to that shown in FIG. 3 but here the stop 2f has a spring 7f whose ends 88 and 89 are extended like the ends of the spring 7e but imbedded in a cylindrical block 85 of synthetic-resin material. Advantageously synthetic-resins are used which are capable of withstanding the high heat of the sterilizer so that if desired the stops can be reused.

It also lies within the scope of the present invention to use a polygonal-section wire to form the springs in order to achieve maximum holding power of the stainless-steel shaft 1. Furthermore, instead of being circularly round in axial profile, the gauge disks or stops can be of any desired shape. This is particularly useful when different spring-holding powers are provided in different stops as the shape and/or color of the stop will indicate its holding characteristics.

I claim:
1. In combination with a shaft of a root-canal tool, a stop, said stop comprising:
    an abutment element formed with a throughgoing hole of larger diameter than said shaft and having an abutment face, said hole defining an axis generally perpendicular to said face; and
    a multiturn coil spring secured to said element and having a throughgoing passage aligned with said axis and having a fully contracted inside diameter slightly smaller than that of said shaft, whereby a shaft fitted axially through said stop is tightly gripped by said spring and said spring is expanded by said shaft.
2. The combination defined in claim 1 wherein said abutment element is formed at said hole with a chamber, said spring being loosely received within said chamber.
3. The combination defined in claim 2 wherein said element is metallic.
4. The combination defined in claim 2 wherein said spring has a pair of outwardly extending arms extending from the terminal turns of said spring and engaging said element.
5. The combination defined in claim 4 wherein said element comprises a pair of parts, one of said arms secured to one of said parts and the other of said arms being engageable by the other of said parts, whereby rotation of said parts relative to each other changes said inner diameter.
6. The combination defined in claim 5 wherein said one part is formed with a slot having a center of curvature at said axis, said other arm engaging in said slot.
7. The combination defined in claim 1 wherein said element is formed of elastically deformable material.
8. The combination defined in claim 7 wherein said spring is imbedded in said element.
9. The combination defined in claim 8 wherein said spring has outwardly extended ends imbedded in said material.
10. The combination defined in claim 8 wherein said element is a block of synthetic-resin material.

* * * * *